(12) United States Patent
Grubbe

(10) Patent No.: US 11,083,853 B2
(45) Date of Patent: Aug. 10, 2021

(54) ROTARY SENSOR ASSEMBLY WITH LOW-POWER FEATURE

(71) Applicant: Novo Nordisk A/S, Bagsvaerd (DK)

(72) Inventor: Mikkel Schouenborg Grubbe, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 328 days.

(21) Appl. No.: 16/063,473

(22) PCT Filed: Dec. 23, 2016

(86) PCT No.: PCT/EP2016/082513
§ 371 (c)(1),
(2) Date: Jun. 18, 2018

(87) PCT Pub. No.: WO2017/114768
PCT Pub. Date: Jul. 6, 2017

(65) Prior Publication Data
US 2018/0369494 A1 Dec. 27, 2018

(30) Foreign Application Priority Data
Dec. 28, 2015 (EP) .................................... 15202797

(51) Int. Cl.
*A61M 5/315* (2006.01)
*G01D 5/252* (2006.01)
*A61M 5/31* (2006.01)

(52) U.S. Cl.
CPC .... *A61M 5/31553* (2013.01); *A61M 5/31568* (2013.01); *A61M 5/31593* (2013.01);
(Continued)

(58) Field of Classification Search
CPC .......... A61M 5/31553; A61M 5/31568; A61M 5/31593; A61M 2005/3126; A61M 2205/52; G01D 5/252
See application file for complete search history.

(56) References Cited

U.S. PATENT DOCUMENTS

| 4,345,240 A | 8/1982 | Amano et al. |
| 5,751,230 A * | 5/1998 | Brandestini .......... G01D 5/2492 341/10 |

(Continued)

FOREIGN PATENT DOCUMENTS

| CN | 101959547 A | 1/2011 |
| CN | 105007964 A | 10/2015 |

(Continued)

*Primary Examiner* — Theodore J Stigell
*Assistant Examiner* — Rachel T. Smith
(74) *Attorney, Agent, or Firm* — Wesley Nicolas

(57) ABSTRACT

A rotary sensor assembly, comprising a first sensor part with a plurality of position sensor segments, and a second sensor part with a grounded contact in contact with a position sensor segment. For a current incremental rotational position a contact is in contact with an un-powered current-position sensor segment, with the neighbour segments being in a powered state. When the contact is rotated to a powered next-position position sensor segment, the next-position sensor segment becomes a new current-position sensor segment. Electronic circuitry is adapted to detect that the new current-position sensor segment is grounded and that the first and second sensor parts thereby have been rotated one increment relative to each other, and subsequently change the state of the former current-position sensor segment from un-powered to powered and the state of the new current-position sensor segment from powered to un-powered.

20 Claims, 6 Drawing Sheets

(52) U.S. Cl.
CPC ..... *G01D 5/252* (2013.01); *A61M 2005/3126* (2013.01); *A61M 2205/52* (2013.01)

(56) References Cited

U.S. PATENT DOCUMENTS

| | | |
|---|---|---|
| 7,008,399 B2 | 3/2006 | Larsen et al. |
| 7,462,787 B1 | 12/2008 | Kang et al. |
| 9,035,663 B2 | 5/2015 | Carley |
| 2009/0318865 A1 | 12/2009 | Moller et al. |
| 2015/0367077 A1 | 12/2015 | Plambech et al. |

FOREIGN PATENT DOCUMENTS

| | | |
|---|---|---|
| DE | 102013218051 A1 | 3/2014 |
| EP | 2275158 A2 | 1/2011 |
| WO | 96/019872 A1 | 6/1996 |
| WO | 2010/052275 A2 | 5/2010 |
| WO | 2013010889 A1 | 1/2013 |
| WO | 2013/083715 A1 | 6/2013 |
| WO | 2014111341 A1 | 7/2014 |
| WO | 2014/128156 A1 | 8/2014 |
| WO | 2014/128157 A1 | 8/2014 |
| WO | 2014128155 | 8/2014 |
| WO | 2015075134 A1 | 5/2015 |
| WO | 2016004329 | 1/2016 |

\* cited by examiner

ROTARY SENSOR ASSEMBLY WITH LOW-POWER FEATURE

CROSS-REFERENCE TO RELATED APPLICATIONS

This application is a 35 U.S.C. § 371 National Stage application of International Application PCT/EP2016/082513 (published as WO 2017/114768), filed Dec. 23, 2016, which claims priority to European Patent Application 15202797.5, filed Dec. 28, 2015, the contents thereof which are incorporated by reference in their entirety.

Rotary Sensor Assembly with Low-Power Feature

The present invention relates to assemblies, devices and systems adapted for capturing information in respect of rotational movement. The invention provides assemblies, devices and systems which are relevant in applications in which energy- and space-efficient design are of importance. In a specific aspect the invention addresses issues relating to electronic dose data capturing in and for a drug delivery device.

BACKGROUND OF THE INVENTION

Rotary sensor assemblies are used in numerous applications in numerous technical fields. In the disclosure of the present invention reference is mostly made to the treatment of diabetes by delivery of insulin using a drug delivery device, however, this is only an exemplary use of the present invention.

Drug delivery devices have greatly improved the lives of patients who must self-administer drugs and biological agents. Drug delivery devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Correspondingly, a number of drug delivery devices with a dose monitoring/acquisition feature has been provided or suggested, see e.g. in US 2009/0318865, WO 2010/052275 and U.S. Pat. No. 7,008,399. However, most devices of today are without it.

When providing a drug delivery with a monitoring feature, a rotary sensor may be incorporated to detect relative movement between components of the drug delivery mechanism, the movement being indicative of a set and/or expelled dose of drug. A traditional rotary sensor is disclosed in e.g. WO 96/19872 comprising a code disc with pick-up code segments and a reference track arranged in two ring-shaped structures as well as a contact structure for each ring structure. One of the ring structures comprises a number of pick-up segments which for a given rotational position is grounded by a metallic rotor member.

Having regard to the above, it is an object of the present invention to provide a drug delivery device as well as components and assemblies therefore which in a safe, user-friendly, power-efficient, cost-effective and reliable way allows detection and storage of dose data related to use of a drug delivery device. It is a further object to provide such components and assemblies which could be used also in other applications having the same types of rotational input.

DISCLOSURE OF THE INVENTION

In the disclosure of the present invention, embodiments and aspects will be described which will address one or more of the above objects or which will address objects apparent from the below disclosure as well as from the description of exemplary embodiments.

In the context of the present invention the term "rotary sensor" also covers similar terms like e.g. "rotational encoder", "rotational position encoder" and "rotary sensor encoder".

Thus, in a first aspect of the invention a rotational encoder assembly is provided comprising a first part with a plurality of position sensor segments each adapted to have a powered and an un-powered state, a second part, rotational in increments relative to the first part, with at least one grounded contact structure adapted to be in contact with a position sensor segment, and electronic circuitry electrically connected to the position sensor segments and adapted to control the power state thereof. For a given current incremental rotational position a contact structure is in contact with an un-powered current-position sensor segment, and at least one neighbour segment to the current-position sensor segment is in a powered state. When the first and second rotary sensor parts are rotated one increment relative to each other, and the contact structure thereby is rotated to a powered next-position position sensor segment, the next-position sensor segment becomes a new current-position sensor segment. The electronic circuitry is adapted to detect a change event in which the new current-position sensor segment is grounded and the first and second sensor parts thereby have been rotated one increment relative to each other, and the electronic circuitry is adapted to subsequently change the state of the former current-position sensor segment from unpowered to powered and the state of the new current-position sensor segment from powered to un-powered.

The term "given current incremental rotational position" is meant to cover normal operational states in which a given switch contact is positioned in contact with a single sensor or reference segment, i.e. outside the gaps formed between two neighbouring sensor segments.

By this arrangement a rotational encoder assembly is provided with active circuitry-controlled power-management. In this way the highest possible resolution for a given incremental sensor can be provided in a power-efficient way as the system can detect a change event for a single index change at any given rotational position. The arrangement also allows an encoder assembly to power-efficiently wake up from a low-power sleep mode to a high-power operational state. As this can be achieved without implementing an additional track for a wakeup feature, a very compact sensor with only a single track of segments is made possible.

In exemplary embodiments the rotational encoder assembly comprises N groups each comprising X corresponding position sensor segments arranged circumferentially on the first part, each group spanning 360/N degrees and comprising a first segment and a last segment, the first and the last segments of a group being controlled as neighbours, and N grounded contact structures circumferentially spaced apart such that for a given incremental rotational position one contact structure will be in contact with the corresponding position sensor segments in each group.

In this way a given number of segments for a full circumferential pattern of 360 degrees can be utilized to provide the desired level of resolution and redundancy. For example, for 24 segments each spanning 15 degrees and N=1 the maximum resolution of 24 positions would be achieved. With N=2 each of the 12 positions within 180 degrees would be represented by two corresponding segments. In an exemplary embodiment the first part comprises at least one ground segment, and the second part comprises at least one ground contact structure electrically connected to the one or more contact structures adapted to be in contact with a position sensor segment.

In alternative exemplary embodiments the rotational encoder assembly comprises N groups each comprising X corresponding position sensor segments arranged circumferentially on the first part, each group spanning 180/N degrees and comprising a first segment and a last segment, the first and the last segments of a group being controlled as neighbours. At least one ground segment is arranged circumferentially on the first part and spans the remaining 180 degrees. The rotational encoder assembly further comprises 2*N electrically connected grounded contact structures spaced 360/(2*N) degrees apart such that for a given incremental rotational position one contact structure will be in contact with the corresponding position sensor segments in each group, and at least one contact structure will be in contact with a ground segment.

With this arrangement both grounding and coding can be combined in a single circumferential pattern, this allowing a compact design. Indeed, for a given size of the position segments the resolution will be lower when half the circumference is used for a ground track. For example, for 12 segments each spanning 15 degrees and N=1 the maximum resolution of 12 positions would be achieved. With N=2 each of the six positions within 90 degrees would be represented by two corresponding segments.

All of the sensor segments which are not in contact with a grounded contact structure may be in a powered state or only one or more of the neighbouring segments. The second rotary sensor part may be in the form of a metallic disc member comprising a plurality of integrally formed flexible arms forming the contact structures.

In the above-described rotary sensor assemblies the electronic circuitry may be operated between a low-power sleep state and a high-power operating state, wherein the electronic circuitry, when a change event is detected with the electronic circuitry in the low-power state, is operated from the low-power sleep state to the high-power operating state.

In an exemplary application the rotary sensor assembly is incorporated cost-effectively and reliably in a drug delivery device comprising a rotational member which rotates corresponding to a set and/or expelled dose.

Correspondingly, in an exemplary embodiment a drug delivery device is provided comprising a rotational encoder assembly as described above, the drug delivery device further comprising a housing, a drug-filled cartridge or means for receiving a drug-filled cartridge, the cartridge comprising an axially displaceable piston and a distal outlet portion, and drug expelling means. The drug expelling means comprises dose setting means allowing a user to set a dose of drug to be expelled, an axially displaceable piston rod adapted to move the piston of a cartridge in a distal direction to thereby expel drug from the cartridge, and an indicator member adapted to rotate corresponding to a set and/or expelled dose, wherein the first and second rotational encoder parts rotate relative to each other during setting and/or expelling of a dose of drug.

In an exemplary embodiment the first part of the rotational encoder assembly is mounted non-rotatably relative to the housing, and the second part of the rotational encoder assembly is mounted to rotate with the indicator member.

The electronic circuitry may be adapted to estimate an amount of expelled drug based on detection of rotational movement between the first and second parts corresponding to a set and/or expelled dose. The electronic circuitry comprises logging means adapted to create a log for dose amounts of drug expelled from a cartridge by the drug expelling means, wherein the dose amounts are calculated based on relative rotation between the first and second rotational encoder parts during setting and/or expelling of a dose of drug. The electronic circuitry may be provided with transmitter means adapted to transmit stored data to an external receiver. Alternatively or in addition, the electronic circuitry may comprise a display adapted to display e.g. the size of an expelled dose and the time since it was expelled.

In order to determine whether a dose is being set or being expelled the drug delivery device may be provided with additional switch arrangements adapted to detect. For example axial switches adapted to detect whether the expelling mechanism is in a dose setting state or an expelling state, this corresponding for example to the axial position of a dose release member. A further switch may be provided to detect when an end-of-dose state has been reached.

Such switches may be incorporated in the first and/or second part of the rotational encoder assembly in the form of additional contact segments on the first part, e.g. in the form of one or more further circumferential rings, and/or additional contact structures on the second part.

In the context of the present application and as used in the specification and the claims, the term electronic circuitry covers any combination of electronic circuitry suitable for providing the specified functionality, e.g. processing and storing data as well as controlling all connected input and output devices. A processor will typically comprise one or more CPUs or microprocessors which may be supplemented by additional devices for support, storage or control functions. For example, in case a communication interface is provided (e.g. wireless), the transmitter and receiver may be fully or partly integrated with a processor, or may be provided by individual units. Each of the components making up the processor circuitry may be special purpose or general purpose devices. The term display means covers any type of display capable of visually providing the specified functionality, e.g. a LCD or an OLED display.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of exemplary embodiments reference will be made to the use of insulin and GLP-1 containing drugs, this including analogues thereof as well as combinations with one or more other drugs.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component. However, the same member or element may alternatively comprise a number of sub-components just as two or more of the described components could be provided as unitary components, e.g. manufactured as a single injection moulded part. The terms "assembly" and "subassembly" do not imply that the described components necessarily can be assembled to provide a unitary or functional assembly or subassembly during a given assembly procedure but is merely used to describe components grouped together as being functionally more closely related.

Figure 1:
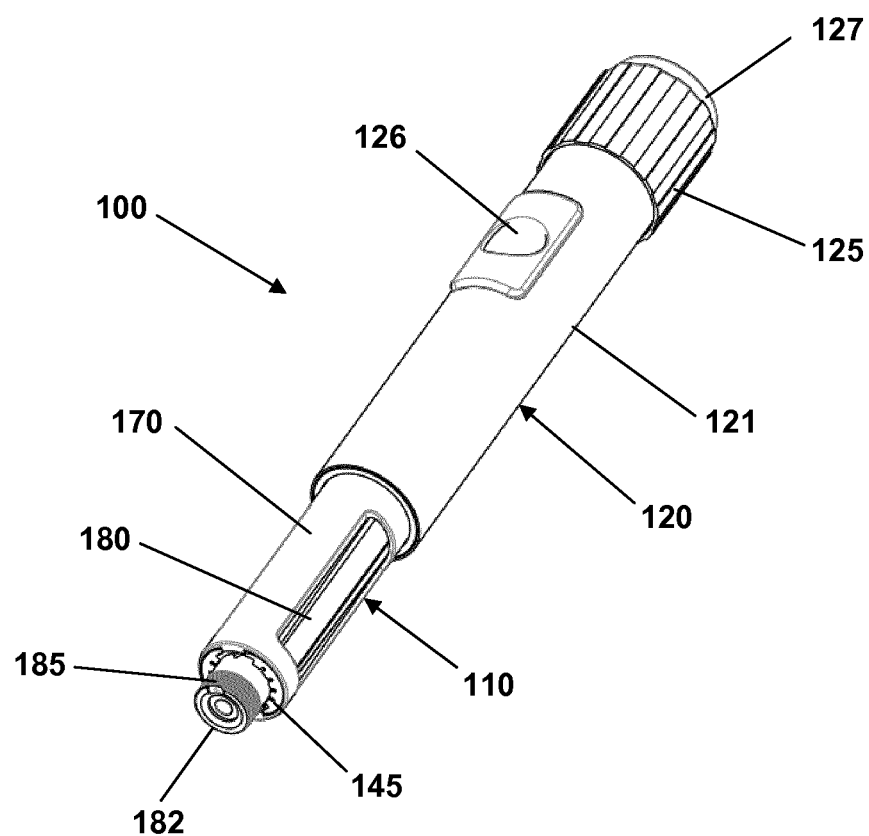
FIGS. 1 and 2 show a front-loaded drug delivery device with and without a drug cartridge mounted, respectively.

Referring to FIG. 1 a pen-formed drug delivery device 100 will be described. The device represents a "generic" drug delivery device providing an example of a device in combination with which embodiments of the present invention is intended to be used, such a device comprising a rotational member adapted to rotate corresponding to a set and/or expelled dose of drug.

More specifically, the pen device comprises a cap part (not shown) and a main part having a proximal body or drive assembly portion 120 with a housing 121 in which a drug expelling mechanism is arranged or integrated, and a distal cartridge holder portion in which a drugfilled transparent cartridge 180 with a distal needle-penetrable septum can be arranged and retained in place by a cartridge holder 110 attached to the proximal portion, the cartridge holder having openings allowing a portion of the cartridge to be inspected. The cartridge may for example contain an insulin, GLP-1 or growth hormone formulation. The device is designed to be loaded by the user with a new cartridge through a distal receiving opening in the cartridge holder, the cartridge being provided with a piston driven by a piston rod 128 forming part of the expelling mechanism. A proximal-most dose setting means in the form of a rotatable dose ring member 125 serves to manually set a desired dose of drug shown in display window 126 and which can then be expelled when the release button 127 is actuated. Depending on the type of expelling mechanism embodied in the drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. The cartridge is provided with distal coupling means in the form of a needle hub mount 182 having, in the shown example, an external thread 185 adapted to engage an inner thread of a corresponding hub of a needle assembly. In alternative embodiments the thread may be combined with or replaced by other connection means, e.g. a bayonet coupling.

Figure 2:
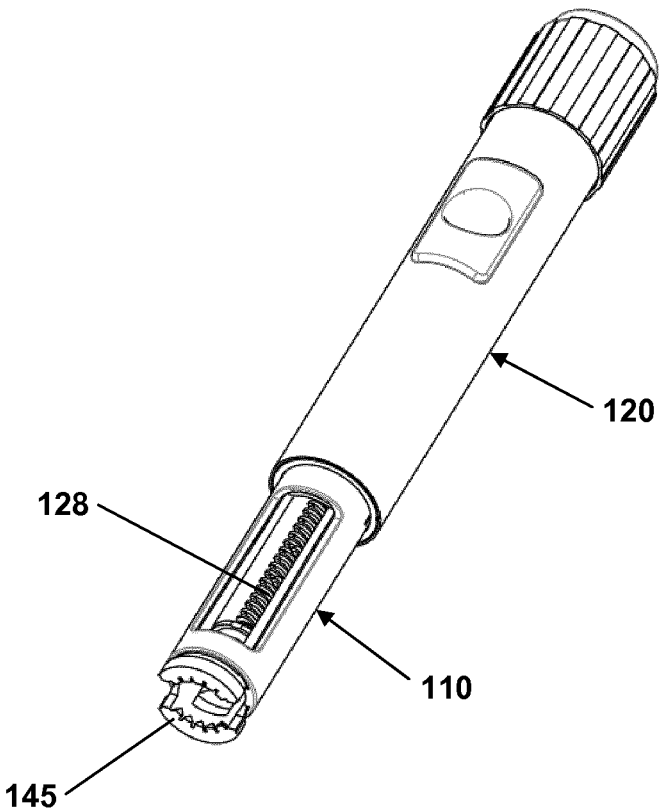

The cartridge holder comprises a distal opening adapted to receive a cartridge. More specifically, the cartridge holder comprises an outer rotatable tube member 170 operated by the user to control movement of gripping means to thereby open and close gripping shoulders 145 configured to grip and hold a cartridge. FIG. 2 shows the device with the cartridge removed and the gripping shoulders in their unlocked "open" position in which a cartridge can be removed and a new inserted.

As appears, FIG. 1 shows a drug delivery device of the front-loaded type in which a cartridge is inserted through a distal opening in the cartridge holder which in non-removable attached to the main part of the device. However, the drug delivery device may alternatively comprise a cartridge holder adapted to be removed from the device main portion and in which a cartridge is received and removed through the proximal opening.

Figure 3:
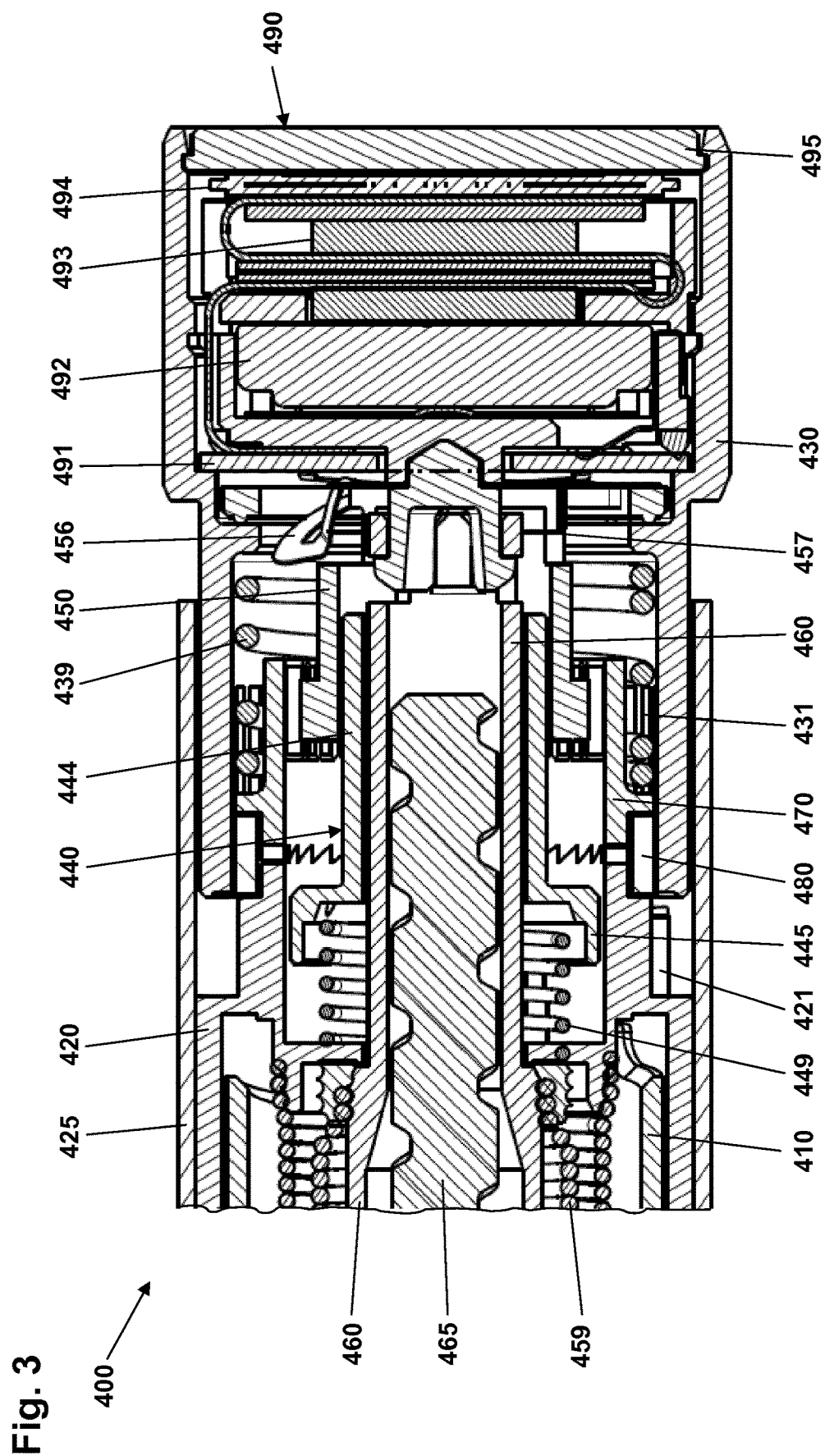
FIG. 3 shows in part a cross-sectional view of a drug delivery device.

FIG. 3 shows the proximal portion of a drug delivery device 400 in a dose setting state, the device comprising a dose button in which a logging module with a rotary sensor assembly is incorporated. The logging module represents a "generic" logging assembly providing an example of a logging assembly in combination with which embodiments of the present invention is intended to be used, such a device comprising a rotational member adapted to rotate corresponding to a set and/or expelled dose of drug.

More specifically, the drug delivery device 400 comprises an inner housing member 420 in which a scale drum 410 is helically guided, a protective outer housing member 425, a piston rod 465, a drive tube 460, a double-wound helical torsion drive spring 459 arranged between the housing and the drive tube, a transmission member 450, a ratchet member 470, a ratchet release member ("lifter") 480, a combined dose setting and release member (dose button) 430, and a dose button return spring 439. The shown embodiment also comprises a trigger member 440 and a trigger spring 449 including tubular portion 444 and distal skirt portion 445, which are described in greater detail in EP application 15176383.6, also published as US 2018/0161503, however, these components are not relevant in the context of the present invention.

In the interior of the dose button a logging module 490 is arranged, the module comprising a distally facing contact disc 491, an electric cell 492, electronic processor circuitry 493, a display 494 and a transparent window 495, all components being non-rotationally arranged in the dose button. A proximally-facing switch disc 455 is non-rotationally attached to the transmission member 450 (see FIG. 4) by e.g. heat stalking as shown, the disc comprising a pair of long-travel mode switch arms 456, a pair of EoD (End of Dose) switch arms 457, and a number of encoder switch arms 458 each having a switch point "dimple" 454 adapted to cooperate with corresponding contact structures on the contact disc 491. The latter two structures 458, 491 together form a rotary sensor assembly whereas the additional switch structures 456, 457 are specific for the shown embodiment of a switch disc. In alternative embodiments the additional switch functionality may not be necessary or it may be incorporated in other structures of the drug delivery device.

The transmission member 450 is mounted axially and rotationally locked to the drive tube 460 and in releasable splined engagement with the ratchet member 470, which is in splined rotationally locked engagement with a circumferential array of dose button splines 431. A unidirectional ratchet interface is provided between the ratchet member 470 and the housing member 420, however, the ratchet release member 480 provides that the ratchet member can be lifted out of engagement with the housing whereby a set dose can be reduced incrementally. The latter arrangement is described in greater detail in EP 15156962.1.

The drive spring 459 is coupled between the housing and the drive tube at its ends, the dose button return spring 439 is supported between the dose button 430 and the ratchet member 470, and the scale drum is rotationally coupled to the drive tube at the distal end (not shown). When setting a dose the dose button 430 is rotated clock-wise, and the coupled ratchet member 470, transmission member 450, drive tube 460, and the scale drum rotate therewith, thereby straining the drive spring 459. Due to the ratchet interface between the ratchet member and the housing member 420 the rotated components are held in the set position. As the dose button 430 and the transmission member 450 rotate together no relative rotational movement is detected by the rotary sensor.

When a dose has been set and the dose button 430 is actuated, the dose button, the transmission member 450 and the drive spring is moved distally. During the initial axial movement the dose button splines 431 engage an outer array of housing splines 421 whereby the dose button is rotationally locked to the housing. At the same time the mode switch arms 456 engage the proximal end of the ratchet member to thereby switch the mode switch in its actuated (closed) mode, i.e. indicating an out-dosing state. At the distal end of the expelling mechanism (not shown) a drive clutch provides that the drive tube 460 is rotationally coupled to a piston rod driver. When the dose button is moved further distally the transmission member 450 disengages the ratchet member, this allowing the strained spring to rotate the drive tube 460 counter-clock-wise, whereby the piston rod driver causes the piston rod 465 to rotate and move distally to expel drug. As the transmission member 450 rotates with the drive tube the rotary sensor detects rotational movement corresponding to the dose amount being expelled. At the same time the scale drum 410 is rotated helically back towards its initial zero position. In the shown embodiment, when the scale drum reaches the zero position an EoD (End of Dose) switch is actuated, this indicating to the logging circuitry that a set dose has been fully expelled, and the dose size corresponding to the detected rotational movement between the transmission member and the dose button.

When pressure on the dose button is released the return spring 439 returns the dose button to its initial proximal position, whereby the EoD (End of Dose) switch re-opens, the transmission member 450 re-engages the ratchet member 470, the drive clutch disengages, the mode switch re-opens and the dose button disengages the housing member.

Having described the general working principle of a "generic" drug delivery device in which a logging module with a rotary sensor assembly is incorporated, an exemplary embodiment of a rotary sensor assembly in accordance with aspects of the present invention will be described.

Figure 5:
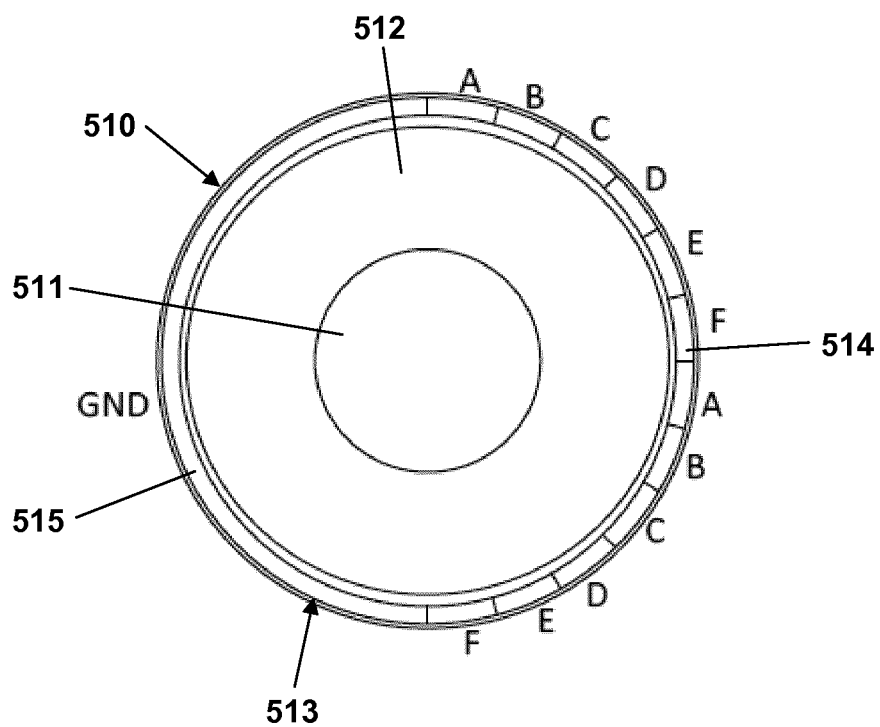
FIG. 5 shows an exemplary contact disc.
Figure 6:
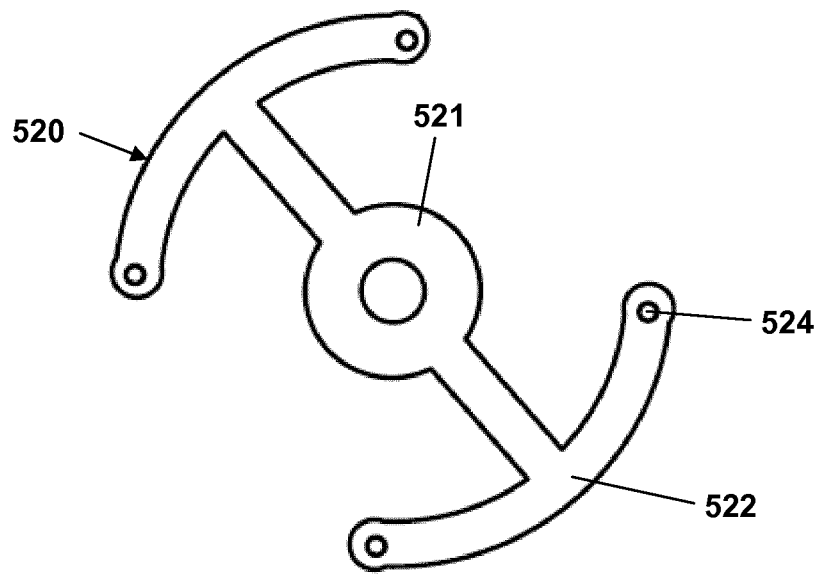
FIG. 6 shows an exemplary switch disc.
Figure 7:
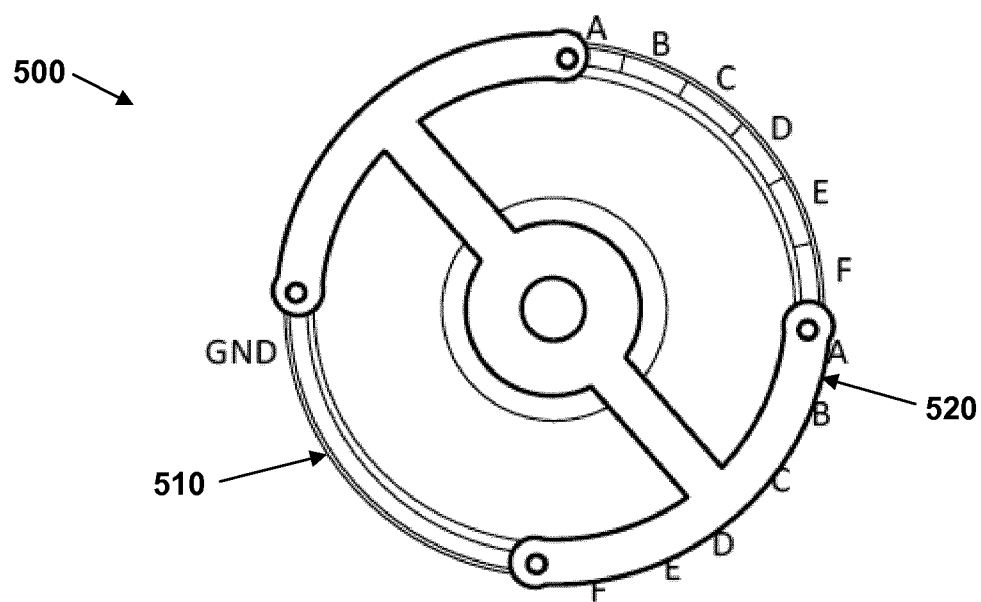
FIG. 7 shows the discs of FIGS. 5 and 6 in an assembled state.

With reference to FIGS. 5-7 a rotational encoder assembly will be described comprising a first rotary sensor portion and a second rotary sensor portion arranged rotationally relative to the first portion.

As shown in FIG. 5 the first rotary sensor portion is in the form of a ring-formed disc 510 with a central opening 511, the disc comprising a surface 512 with a circumferential ring pattern 513 of contact segments. In the shown embodiment the ring comprises 12 individual electrically conducting rotational position code sensor segments 514, each sensor segment spanning 15 degrees for a total of 180 degrees, as well as a single ground segment 515 (labelled GND) spanning the remaining 180 degrees. Alternatively the ground segment could be divided in a number of grounded segments. The 12 sensor segments form two groups of 6 segments labelled A-F and adapted to be connected to associated electronic circuitry to provide for a 6 bit code (A-F) and a total of 24 incremental positions, e.g. corresponding to 24 incremental positions for a full rotation of a dose setting 125, 430.

As shown in FIG. 6 the second rotary sensor portion is in the form of a switch disc 520 formed from a conducting material, e.g. metal, and comprising a central mounting portion 521 from which two anchor-like structures protrude radially to provide a total of 4 contact arms 522 with a free end, each arm comprising a dimple-formed contact point 524 located in the proximity of the free end and being adapted to slidingly engage and establish electrical contact with the segments of the individual contact segments as the two discs rotate relative to each other. The 4 contact points are arranged with a 90 degrees spacing between two neighbouring points.

As shown in FIG. 7, when the two discs 510, 520 are rotationally mounted relative to each other, the size and spacing of the sensor segments respectively the spacing of the contact points ensure that for any rotational position two contact points are positioned on two corresponding position sensor segments, for example, the two A position segments as shown, and two contact points are positioned on the ground segment. In this way it ensured that redundancy is provided for both the position segments and the ground contacts. Indeed, the 12 position sensor segments in combination with two contact points could be used to provide a 12 bit code without redundancy, or alternatively the 12 position sensor segments in combination with 6 contact points could be used to provide a 4 bit code with triple redundancy.

When connected to associated electronic circuitry (not shown) each position sensor segment is either in a powered on-state "1" or in an un-powered off-state "0". For a given current incremental rotational position two contact points are in contact with a pair of corresponding un-powered current-position sensor segment, e.g. the two A segments as shown in FIG. 7, and two contact points are in contact with the ground segment thereby connecting the two current-position sensor segments and the ground segment. The remaining position sensor segments B-F are in a powered state, however, the described sensor concept would also function if only one neighbour segment for any given current segment were powered, this allowing detection of rotational movement in one direction. Correspondingly, if both neighbour segments for any given current segment were powered, this would allow detection of rotational movement in both directions. For the shown embodiment with a group of segments A-F spanning less than 360 degrees the neighbour segments of e.g. segment F are segments E and A. Indeed, for a short period of time during rotation a given switch contact point will bridge two neighbouring position sensor segments.

When the first and second rotary sensor portions are rotated relative to each other, e.g. the switch disc 520 is rotated relative to the sensor disc 510, the two contact points former positioned on the A segments are rotated to the powered next-position position sensor segments B which becomes a new current-position sensor segment. The electronic circuitry is adapted to (i) detect that the new current-position sensor segments B are grounded and thereby that the first and second rotary sensor portions are rotated one increment relative to each other, and to (ii) subsequently change the state of the former current-position sensor segment from un-powered to powered and the state of the new current-position sensor segment from powered to un-powered. The detection of an incremental change of position is used as input to count the number of incremental changes, e.g. corresponding to the increments of a dose set. The 6 bit resolution allows the circuitry to register movement in both directions just as a skipped position can be compensated for, e.g. if the sensor shifts from position A to C two increments will be detected and counted.

Figure 8:
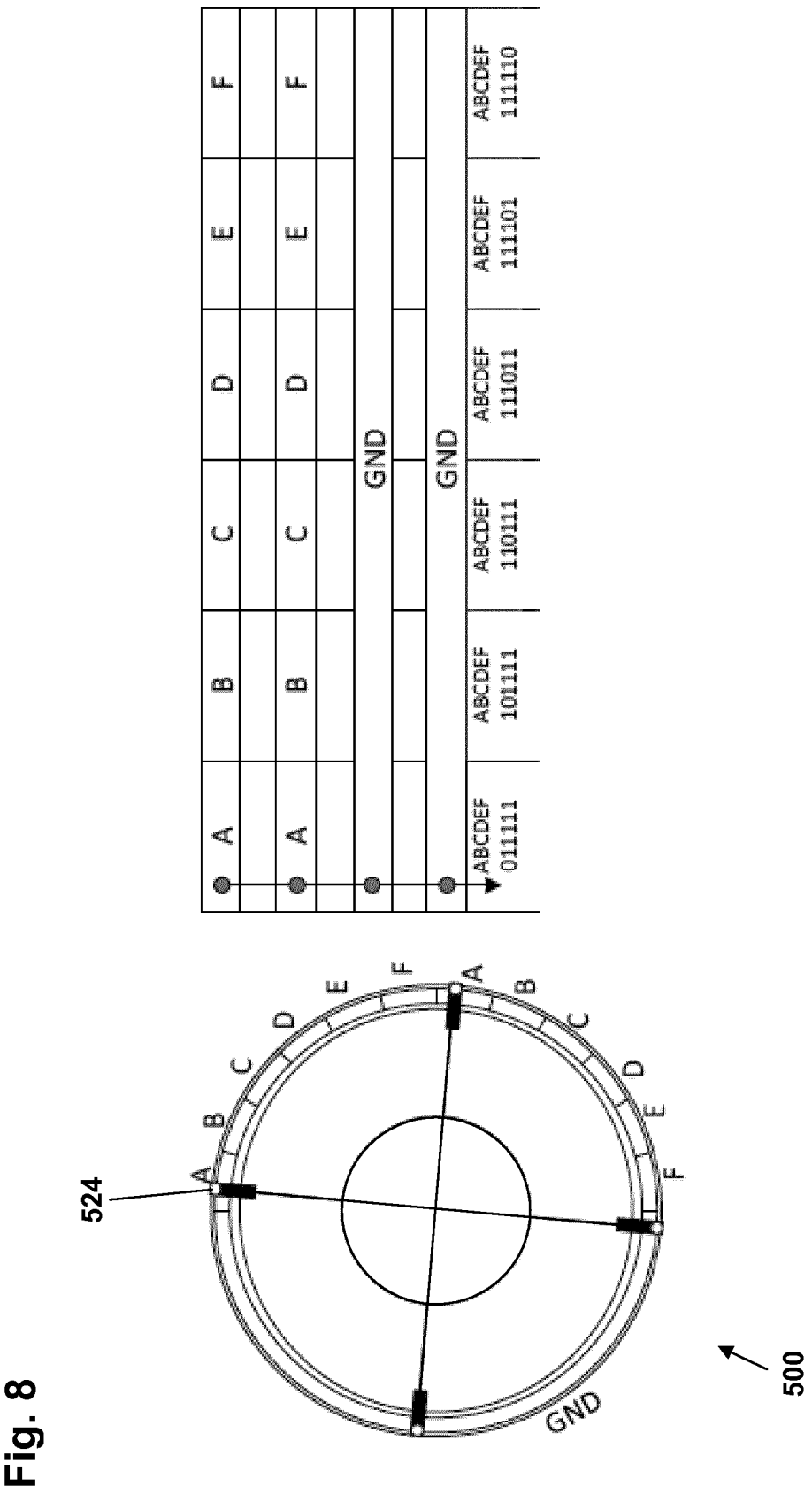
FIG. 8 shows schematically the different possible codes for the assembly of FIG. 7.

FIG. 8 illustrates schematically the different possible codes for the 6 incremental positions for the four switch disc contact points 524. For example, with the switch disc contact points positioned on the position sensor segments A the detected states for the two pairs of 6 segments A-F are 011111. When the switch disc is rotated to position B the states 101111 are detected for the segments A-F and so forth.

Figure 9:
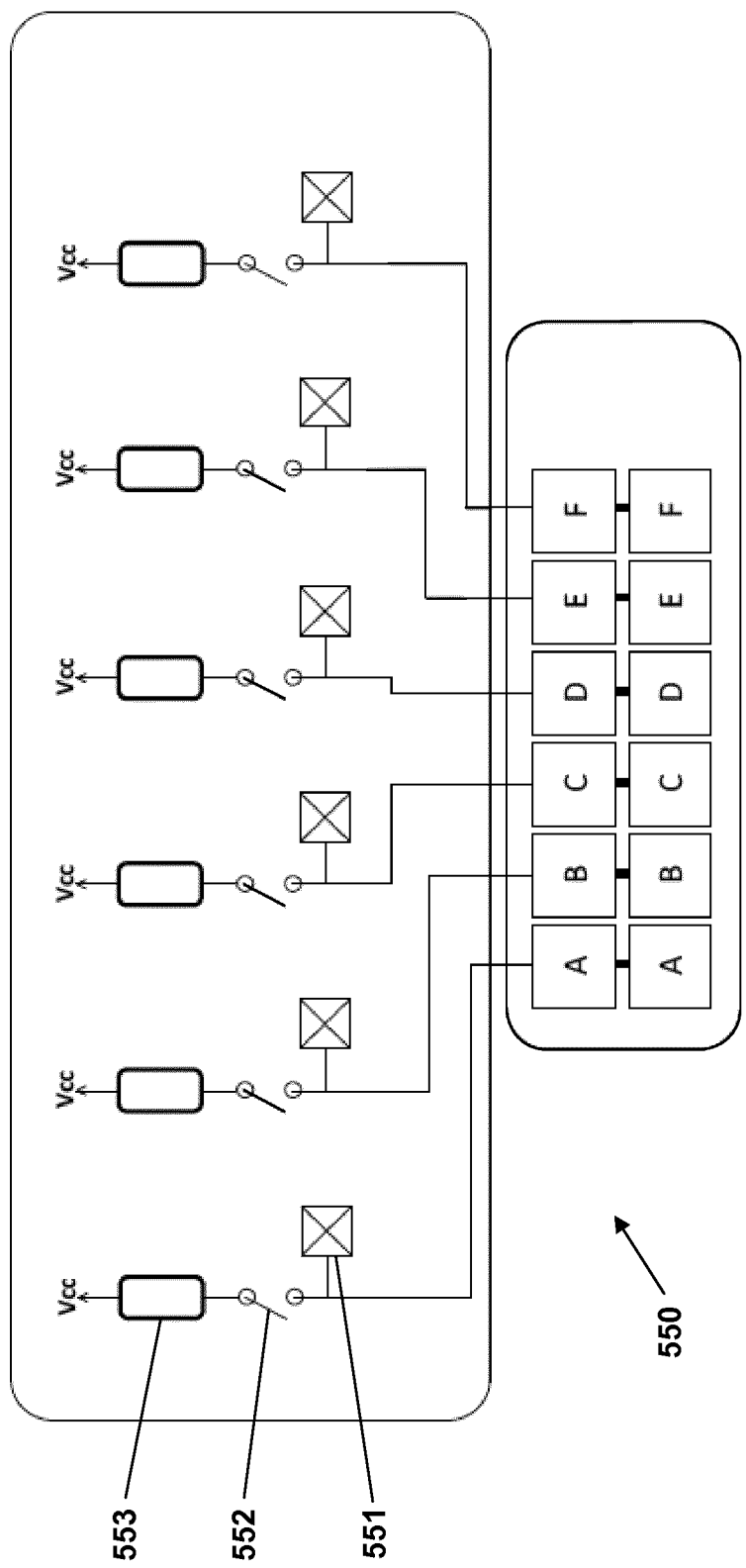
FIG. 9 shows schematically the position code segments and microcontroller interface.

FIG. 9 shows schematically the position code segments and microcontroller (MCU) interface 550. The pairs of corresponding position segments A-F are each connected to switch circuitry comprising an input terminal 551 for a micro controller, a switch 552, a pull-up resistor 553 and a MCU power supply input Vcc.

The above-described concept makes it possible to provide the highest possible resolution for a given incremental sensor as the system can wake up from a low-power sleep mode to an operational state for a single index change at any given rotational position. As this is achieved without implementing an additional track for a wake-up feature, a very compact sensor with only a single track of segments is provided.

In the shown and described embodiment the disc 510 comprises a single circumferential ring pattern 513 of contact segments providing both rotational position code sensor segments and a ground segment. In alternative embodiments the entire ring pattern may be used for position code sensor segments and the grounding of the contact structures may be established in alternative ways, e.g. by a separate circumferential ground track.

Figure 4:
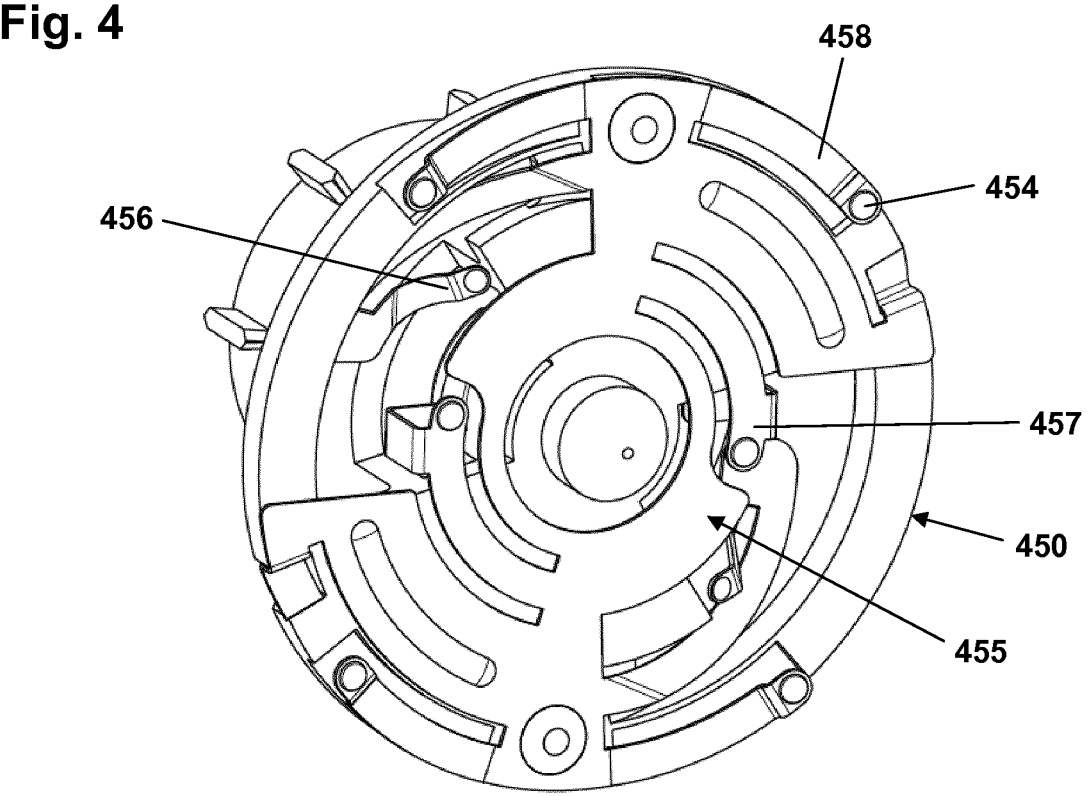
FIG. 4 shows the switch disc incorporated in the device of FIG. 3.

As described with reference to FIGS. 3 and 4, in order to determine whether a dose is being set or being expelled, the drug delivery device may be provided with additional switch arrangements adapted to detect for example axial switches adapted to detect whether the expelling mechanism is in a dose setting state or an expelling state, this corresponding for example to the axial position of a dose release member. A further switch may be provided to detect when an end-of-dose state has been reached.

Such switches may be incorporated in the first and/or second part of the rotational encoder assembly shown in FIGS. 5-7 in the form of additional contact segments on the first part, e.g. in the form of one or more further circumferential rings, and/or additional contact structures on the second part.

In the above description of exemplary embodiments, the different structures and means providing the described functionality for the different components have been described to a degree to which the concept of the present invention will be apparent to the skilled reader.

The detailed construction and specification for the different components are considered the object of a normal design procedure performed by the skilled person along the lines set out in the present specification.

The invention claimed is:

1. A rotary sensor assembly, comprising:
   a first sensor part with a plurality of position sensor segments, each adapted to have a powered and an un-powered state,
   a second sensor part, rotational in increments relative to the first part, with at least one grounded contact structure adapted to be in contact with one of the plurality of position sensor segments, and
   electronic circuitry electrically connected to the plurality of position sensor segments and adapted to control the powered and un-powered states,
   wherein:
   for a current incremental rotational position, one of the at least one grounded contact structure(s) is in contact with an un-powered current-position sensor segment,
   at least one neighbour segment of the plurality of position sensor segments to the un-powered current-position sensor segment is in the powered state,
   when the first and second sensor parts are rotated one increment relative to each other, and one of the at least one grounded contact structure(s) thereby is rotated to a powered next-position sensor segment, the powered next-position sensor segment becomes a new current-position sensor segment,
   the electronic circuitry is adapted to detect a change event in which the new currentposition sensor segment is grounded and the first and second sensor parts thereby have been rotated one increment relative to each other, and
   the electronic circuitry is adapted to subsequently change the state of the unpowered current-position sensor segment from un-powered to powered and the state of the new current-position sensor segment from powered to un-powered,
   wherein the sensor assembly further comprises:
   N groups each comprising X corresponding position sensor segments of the plurality of position sensor segments arranged circumferentially on the first sensor part, each one of the N groups spanning 180/N degrees and comprising a first segment and a last segment, the first and the last segments of one of the N groups being controlled as neighbours, at least one ground segment arranged circumferentially on the first sensor part and spanning 180 degrees, and 2*N of the at least one grounded contact structure(s) spaced 360/(2*N) degrees apart such that for a given incremental rotational position one of the at least one grounded contact structure(s) will be in contact with the corresponding position sensor segments in each one of the N groups, and one of the at least one grounded contact structure(s) will be in contact with one of the at least one ground segment(s).

2. The rotary sensor assembly as in claim 1, comprising:

N groups each corresponding to the plurality of position sensor segments arranged circumferentially on the first sensor part, each group spanning 360/N degrees and comprising a first segment and a last segment, the first and the last segments of one of the N groups being controlled as neighbours, and the at least one grounded contact structure(s) circumferentially spaced apart such that for a given incremental rotational position the at least one grounded contact structure(s) will be in contact with the corresponding plurality of position sensor segments in each one of the N groups.

3. The rotary sensor assembly as in claim 1, wherein the plurality of position sensor segments which are not in contact with the at least one grounded contact structure(s) are in the powered state.

4. The rotary sensor assembly as in claim 1, wherein:

the electronic circuitry is configured to be operated between a low-power sleep state and a high-power operating state, and the electronic circuitry, when the change event is detected with the electronic circuitry in the low-power sleep state, is changed from the low-power sleep state to the high-power operating state.

5. A drug delivery device comprising:

a rotary sensor assembly as in claim 1, a housing, a drug-filled cartridge or structure for receiving the drug-filled cartridge, the drugfilled cartridge comprising an axially displaceable piston rod and a distal outlet portion, and a drug expelling structure comprising:

dose setting structure allowing a user to set a dose of drug to be expelled, a piston rod driver adapted to move the piston of the drug-filled cartridge in a distal direction to thereby expel the dose of drug to be expelled from the cartridge, and an indicator member adapted to rotate corresponding to a set and/or expelled dose of the drug to be expelled, wherein:

the first and second sensor parts rotate relative to each other during setting and/or expelling of the dose of drug to be expelled.

6. The drug delivery device as in claim 5, wherein the first sensor part is mounted non-rotatably relative to the housing, and the second sensor part is mounted non-rotatably relative to the indicator member.

7. The drug delivery device as in claim 5, wherein the electronic circuitry is adapted to estimate an amount of expelled drug based on detection of rotational movement between the first and second sensor parts corresponding to the set and/or expelled dose.

8. The drug delivery device as in claim 5, wherein the electronic circuitry comprises logging structure adapted to create a log for dose amounts of the drug expelled from the drug-filled cartridge by the drug expelling structure, wherein the dose amounts are calculated based on relative rotation between the first and second sensor parts during the setting and/or expelling the dose of drug to be expelled.

9. The drug delivery device as in claim 5, wherein the first sensor part comprises a further contact segment and the second sensor part comprises a further contact structure adapted to be in contact with further contact segment, with the further contact segment and the further contact structure forming a switch, the switch being actuatable between a first state in which the further contact structure is not in contact with the further contact segment, and a second state in which the further contact structure is in contact with the further contact segment.

10. The drug delivery device as in claim 5, wherein the electronic circuitry comprises a display.

11. A rotary sensor assembly, comprising:

a first sensor part with a plurality of position sensor segments, each adapted to have a powered and an un-powered state, a second sensor part, rotational in increments relative to the first part, with at least one grounded contact structure adapted to be in contact with one of the plurality of position sensor segments, and electronic circuitry electrically connected to the plurality of position sensor segments and adapted to control the powered and un-powered states, wherein:

for a current incremental rotational position, one of the at least one grounded contact structure(s) is in contact with an un-powered current-position sensor segment, at least one neighbour segment of the plurality of position sensor segments to the un-powered current-position sensor segment is in the powered state, when the first and second sensor parts are rotated one increment relative to each other, and one of the at least one grounded contact structure(s) thereby is rotated to a powered next-position sensor segment, the powered next-position sensor segment becomes a new current-position sensor segment, the electronic circuitry is adapted to detect a change event in which the new currentposition sensor segment is grounded and the first and second sensor parts thereby have been rotated one increment relative to each other, and the electronic circuitry is adapted to subsequently change the state of the unpowered current-position sensor segment from un-powered to powered and the state of the new current-position sensor segment from powered to un-powered, and the electronic circuitry is configured to be operated between a low-power sleep state and a high-power operating state, and the electronic circuitry, when the change event is detected with the electronic circuitry in the low-power sleep state, is changed from the low-power sleep state to the high-power operating state.

12. The rotary sensor assembly as in claim 11, comprising:

N groups each corresponding to the plurality of position sensor segments arranged circumferentially on the first sensor part, each group spanning 360/N degrees and comprising a first segment and a last segment, the first and the last segments of one of the N groups being controlled as neighbours, and the at least one grounded contact structure(s) circumferentially spaced apart such that for a given incremental rotational position the one of the at least one grounded contact structure(s) will be in contact with the corresponding plurality of position sensor segments in each one of the N groups.

13. The rotary sensor assembly as in claim 11, comprising:
N groups each comprising X corresponding position sensor segments of the plurality of position sensor segments arranged circumferentially on the first sensor part, each one of the N groups spanning 180/N degrees and comprising a first segment and a last segment, the first and the last segments of one of the N groups being controlled as neighbours,
at least one ground segment arranged circumferentially on the first sensor part and spanning 180 degrees, and
2*N of the at least one grounded contact structures spaced 360/(2*N) degrees apart such that for a given incremental rotational position one of the at least one grounded contact structure(s) will be in contact with the corresponding plurality of position sensor segments in each one of the N groups, and one of the at least one grounded contact structure(s) will be in contact with one of the at least one ground segment(s).

14. The rotary sensor assembly as in claim 11, wherein the plurality of position sensor segments which are not in contact with the at least one grounded contact structure(s) are in the powered state.

15. A drug delivery device comprising:
a rotary sensor assembly as in claim 11,
a housing,
a drug-filled cartridge or structure for receiving the drug-filled cartridge, the drugfilled cartridge comprising an axially displaceable piston rod and a distal outlet portion, and
a drug expelling structure comprising:
dose setting structure allowing a user to set a dose of drug to be expelled,
a piston rod driver adapted to move the piston of the drug-filled cartridge in a distal direction to thereby expel the dose of drug to be expelled from the cartridge, and
an indicator member adapted to rotate corresponding to a set and/or expelled dose of the drug to be expelled,
wherein:
the first and second sensor parts rotate relative to each other during setting and/or expelling of the dose of drug to be expelled.

16. The drug delivery device as in claim 15, wherein the first sensor part is mounted non-rotatably relative to the housing, and the second sensor part is mounted non-rotatably relative to the indicator member.

17. The drug delivery device as in claim 15, wherein the electronic circuitry is adapted to estimate an amount of expelled drug based on detection of rotational movement between the first and second sensor parts corresponding to the set and/or expelled dose.

18. The drug delivery device as in claim 15, wherein the electronic circuitry comprises logging structure adapted to create a log for dose amounts of the drug expelled from the drug-filled cartridge by the drug expelling structure, wherein the dose amounts are calculated based on relative rotation between the first and second sensor parts during the setting and/or expelling the dose of drug to be expelled.

19. The drug delivery device as in claim 15, wherein the first sensor part comprises a further contact segment and the second sensor part comprises a further contact structure adapted to be in contact with further contact segment, with the further contact segment and the further contact structure forming a switch, the switch being actuatable between a first state in which the further contact structure is not in contact with the further contact segment, and a second state in which the further contact structure is in contact with the further contact segment.

20. The drug delivery device as in claim 15, wherein the electronic circuitry comprises a display.

* * * * *

UNITED STATES PATENT AND TRADEMARK OFFICE
CERTIFICATE OF CORRECTION

PATENT NO. : 11,083,853 B2
APPLICATION NO. : 16/063473
DATED : August 10, 2021
INVENTOR(S) : Mikkel Schouenborg Grubbe It is certified that error appears in the above-identified patent and that said Letters Patent is hereby corrected as shown below:

In the Claims

At Column 13, Claim number 13, Line number 20, please replace:
"structures"
With:
"structure(s),"

Signed and Sealed this
First Day of March, 2022

Drew Hirshfeld
*Performing the Functions and Duties of the*
*Under Secretary of Commerce for Intellectual Property and*
*Director of the United States Patent and Trademark Office*